(12) United States Patent
Kayano et al.

(10) Patent No.: US 6,642,377 B1
(45) Date of Patent: Nov. 4, 2003

(54) PROCESS FOR THE PREPARATION OF BASIC ANTIBIOTIC-INORGANIC ACID ADDITION SALTS AND INTERMEDIATE OXALATES

(75) Inventors: Akio Kayano, Ibaraki (JP); Hiroyuki Chiba, Ibaraki (JP); Taiju Nakamura, Ibaraki (JP); Shin Sakurai, Chiba (JP); Hiroyuki Ishizuka, Ibaraki (JP); Hiroyuki Saito, Ibaraki (JP); Yuuki Komatsu, Ibaraki (JP); Manabu Sasho, Ibaraki (JP); Nobuaki Sato, Ibaraki (JP); Shigeto Negi, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 10/030,909

(22) PCT Filed: Jul. 27, 2000

(86) PCT No.: PCT/JP00/05031
§ 371 (c)(1),
(2), (4) Date: Jan. 14, 2002

(87) PCT Pub. No.: WO01/09135
PCT Pub. Date: Feb. 8, 2001

(30) Foreign Application Priority Data

Jul. 30, 1999 (JP) .......................................... 11-216806
Jul. 30, 1999 (JP) .......................................... 11-216807

(51) Int. Cl.$^7$ .................. C07D 477/20; C07D 501/36; C07D 501/46; C07D 501/22; C07D 499/68
(52) U.S. Cl. .................. 540/222; 540/225; 540/227; 540/228; 540/314; 540/328; 540/350
(58) Field of Search ................ 540/328, 314, 540/228, 222, 225, 227, 350

(56) References Cited

U.S. PATENT DOCUMENTS 3,869,449 A * 3/1975 Godtfredsen ................ 540/312
5,302,711 A    4/1994 Fisher et al.

FOREIGN PATENT DOCUMENTS

| EP | 773222 | 5/1997 |
|---|---|---|
| EP | 773222 A1 | 5/1997 |
| EP | 1 182 204 A1 | 2/2002 |
| JP | 4-41489 | 2/1992 |
| JP | 4-41489 A | 2/1992 |
| JP | 8-73462 A | 3/1996 |
| WO | 94/10177 | 5/1994 |
| WO | 94/10177 A1 | 5/1994 |

OTHER PUBLICATIONS

Webster's new 20$^{th}$ century Dictionary of the English Language, 1979, p. 1545.*
Merck Index, 13$^{th}$ edition, p. THER–5, THER–6.*

* cited by examiner

*Primary Examiner*—Mark L. Berch
(74) *Attorney, Agent, or Firm*—Birch, Stewart, Kolasch & Birch, LLP

(57) ABSTRACT

A production process which comprises subjecting a basic antibiotic·oxalate (II) to salt-exchange with an alkali earth metal salt (III) of an inorganic acid:

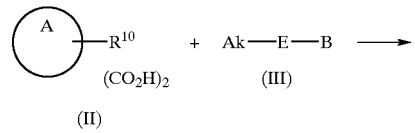

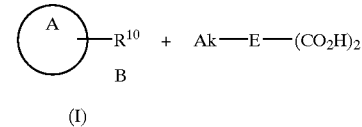

wherein the ring A means the basic antibiotic; $R^{10}$ means a protected functional group used in organic synthesis; Ak—E means the alkali earth metal; and B means the inorganic acid, respectively.

13 Claims, No Drawings

PROCESS FOR THE PREPARATION OF BASIC ANTIBIOTIC-INORGANIC ACID ADDITION SALTS AND INTERMEDIATE OXALATES

This, application is the national phase under 35 U.S.C. §371 of PCT International Application No. PCT/JP00/05031 which has an International filing date of Jul. 27, 2000, which designated the United States of America.

FIELD OF THE INVENTION

The present invention relates to a novel and industrially-excellent process for producing a basic antibiotic.inorganic acid salt. For example, herein described is an industrially-excellent production process for producing an inorganic acid salt of an excellent antimicrobial agent having strong antimicrobial action on gram-positive bacteria and gram-negative bacteria, disclosed in JP-A 8-73462. More specifically, it relates to an industrially-excellent production process for producing, for example, (1R,5S,6S)-6-[(R)-1-hydroxyethyl]-1-methyl-2-{(2S,4S)-2-[(3R)-pyrrolidine-3-yl-(R)-hydroxy]methyl}pyrrolidine-4-ylthio]-1-carbapen-2-em-3-carboxylic acid.hydrochloride, a novel oxalate useful as a production intermediate, and a process for producing it.

PRIOR ART

In order to produce a basic antibiotic.inorganic acid salt, it is generally known to produce a free form, purify by column chromatography etc., and react the product with an inorganic acid.

For example, in the process disclosed in JP-A 8-73462, WO96/01261 or Example 9 of EP-A 773222 as a process for producing (1R,5S,6S)-6-[(R)-1-hydroxyethyl]-1-methyl-2-{(2S,4S)-2-[(3R)-pyrrolidine-3-yl-(R)-hydroxy]methyl}pyrrolidine-4-ylthio]-1-carbapen-2-em-3-carboxylic acid.hydrochloride etc., the objective product is obtained by subjecting a p-nitrobenzyl ester compound to catalytic reduction, purifying by reversed-phase silica gel chromatography, converting the product to a hydrochloride, and subjecting it to freeze-drying.

In the above-mentioned process in the prior art, the purification by chromatography is performed. Thus, a solvent is used in a large amount. Therefore, costs for the production rise to a considerable degree. Additionally, many problems as follows arise: difficulty in industrial processing in large amounts, the possibility of generating thermal cruelty (thermal decomposition) at the time of concentrating fractions, solvent remaining in the final product, disposal of waste liquid and environment pollution due to transpiration of the solvent. Thus, it cannot be said that the process is suitable for industry.

Moreover, it is necessary to perform subtle adjustment of pH when the free form is produced (neutralized) or converted to the hydrochloride. Thus, the process requires much labor and cost in industrial production. Moreover, freeze-drying is required in the last step, and results additional problems as follows: a further rise in the production costs, unsuitability thereof for processing in large amount and necessity of much

DISCLOSURE OF THE INVENTION

Thus, the present inventors made eager investigations to pursue a novel production process excellent in viewpoints such as production costs, operability (workability, safety and non-toxicity), the purity of final products, and the protection of the environment.

As a result, they have found out that the above-mentioned problems can be overcome at a stroke by using a novel oxalate (which will be in detail described below) as a production intermediate, and subjecting the oxalate to salt-exchange with an alkali earth metal salt an inorganic acid. Thus, they have accomplished the present invention.

Therefore, an object of the present invention is to provide a novel production process useful for producing a basic antibiotic.inorganic acid salt industrially, and a novel production intermediate useful for producing antimicrobial agents, and a process for producing it.

In one embodiment, the present invention is a process for producing a basic antibiotic.inorganic acid salt (I), which comprises subjecting a basic antibiotic.oxalate (II) to salt-exchange with an alkali earth metal salt (III) of an inorganic acid.

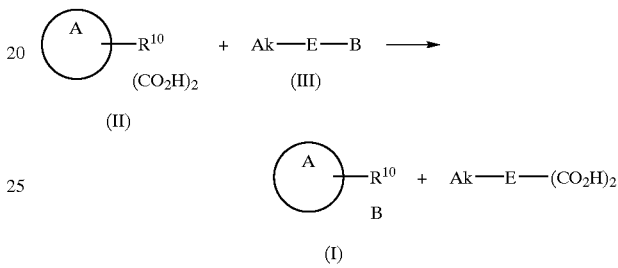

wherein the ring A means the basic antibiotic; $R^{10}$ means a protected functional group used in organic synthesis; Ak—E means the alkali earth metal; and B means the inorganic acid.

In another embodiment, the present invention is a process for producing a basic antibiotic.inorganic acid salt (I), which comprises subjecting a basic antibiotic protector.oxalate (VI) to deprotection reaction; and then subjecting to salt-exchange with an alkali earth metal salt (III) of an inorganic acid. The present invention is also a process for producing a basic antibiotic.inorganic acid salt (I), which comprises subjecting a basic antibiotic protector.oxalate (VI) to deprotection reaction; then subjecting to salt-exchange with an alkali earth metal salt (III) of an inorganic acid; and then crystallizing the resultant or resulting compound by adding a poor solvent thereto.

The present invention is also a process for producing (1R,5S,6S)-6-[(R)-1-hydroxyethyl]-1-methyl-2-{(2S,4S)-2-[(3R)-pyrrolidine-3-yl-(R)-hydroxy]methyl}pyrrolidine-4-ylthio]-1-carbapen-2-em-3-carboxylic acid.hydrochloride (VIII) represented by the following formula:

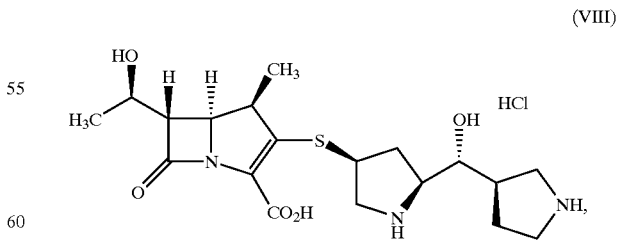

which comprises subjecting p-nitrobenzyl(1R,5S,6S)-6-[(R)-1-hydroxyethyl]-1-methyl-2-{(2S,4S)-2-[(3R)-pyrrolidine-3-yl-(R)-hydroxy]methyl}pyrrolidine-4-ylthio]-1-carbapen-2-em-3-carboxylate.oxalate (VII) represented by the following formula:

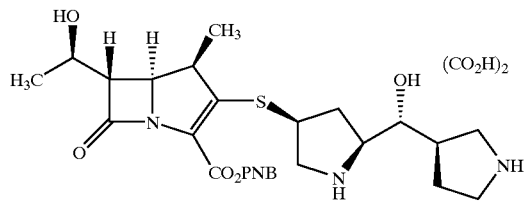
(VII)

(wherein PNB represents p-nitrobenzyl group) to deprotection reaction; then subjecting to salt-exchange with calcium chloride; and then crystallizing the resulting compound by adding methanol and/or isopropanol thereto.

The present invention is a process for producing a basic antibiotic·inorganic acid salt (I), in which the oxalate (II-I) of a carbapenem compound represented by the following formula is a basic antibiotic·oxalate (II), and which comprises subjecting the basic antibiotic·oxalate (II) to salt-exchange with an alkali earth metal salt (III) of an inorganic acid.

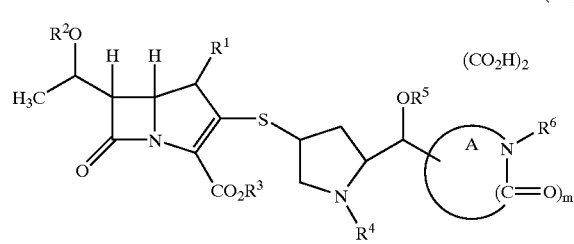
(II-I)

The ring A represents a 3- to 7-membered ring having at least one nitrogen atom, and the ring A may be substituted with other than $R^6$; $R^1$ represents hydrogen or methyl group; $R^2$ and $R^5$ are the same as or different from each other and each represents hydrogen or a hydroxyl-protecting group; $R^3$ represents a carboxyl-protecting group; $R^4$ represents hydrogen, a lower alkyl group or an amino-protecting group; $R^6$ represents (1) hydrogen, (2) an optionally protected hydroxyl group, carbamoyl, formimidoyl, acetoimidoyl or a lower alkyl group which may be substituted with a substituent represented by the formula:

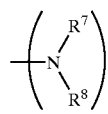

(wherein $R^7$ and $R^8$ are the same as or different from each other and each represents hydrogen, a lower alkyl group or an amino-protecting group) or (3) an amino-protecting group or an imino-protecting group; and m is 0 or 1.

The present invention is an oxalate (II-I) of a carbapenem compound represented by the following formula:

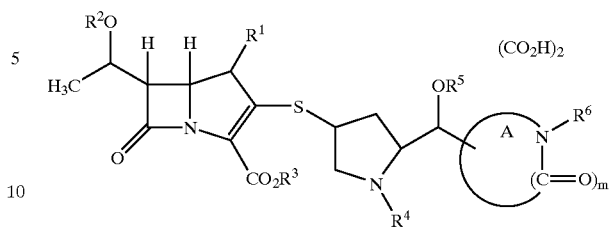
(II-I)

wherein the ring A represents a 3- to 7-membered ring having at least one nitrogen atom, and the ring A may be substituted with other than $R^6$; $R^1$ represents hydrogen or methyl group; $R^2$ and $R^5$ are the same as or different from each other and each represents hydrogen or a hydroxyl-protecting group; $R^3$ represents a carboxyl-protecting group; $R^4$ represents hydrogen, a lower alkyl group or an amino-protecting group; $R^6$ represents (1) hydrogen, (2) an optionally protected hydroxyl group, carbamoyl, formimidoyl, acetoimidoyl or a lower alkyl group which may be substituted with a substituent represented by the formula:

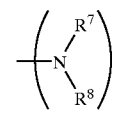

(wherein $R^7$ and $R^8$ are the same as or different from each other and each represents hydrogen, a lower alkyl group or an amino-protecting group) or (3) an amino-protecting group or an imino-protecting group; and m is 0 or 1.

Further, the present invention is a process for producing p-nitrobenzyl(1R,5S,6S)-6-[(R)-1-hydroxyethyl]-1-methyl-2-{(2S,4S)-2-[(3R)-pyrrolidine-3-yl-(R)-hydroxy]methyl}pyrrolidine-4-ylthio]-1-carbapen-2-em-3-carboxylate·oxalate (II-III), which comprises reacting p-nitrobenzyl(1R,5S,6S)-6-[(R)-1-hydroxyethyl]-1-methyl-1-carbapen-2-em-3-carboxylate-2-active compound (XIV) represented by the following formula:

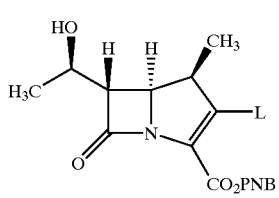
(XIV)

(wherein PNB has the same meaning as described above; and L means a leaving group) with (2S,4S)-2-{[(3R)-pyrrolidine-3-yl-(R)-hydroxy]methyl}-4-mercaptopyrrolidine·dihydrochloride (XV) represented by the following formula:

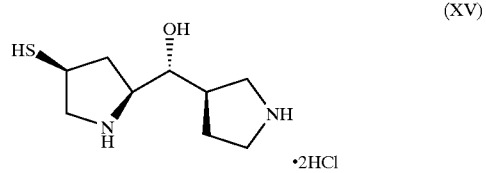
(XV)

and then converting the resultant into to an oxalate.

Herein, the basic antibiotic.inorganic acid salt (I) according to the present invention is an antibiotic having a basic salt in the molecule thereof, and is not limited so long as the antibiotic is combined with an inorganic acid to form a salt. Preferred examples thereof include the following:

(1) cefotiam (CAS Res.No.: 66309-69-1) hydrochloride;
(2) cefmenoxime (CAS Res.No.: 75738-58-8) hydrochloride;
(3) cefozopran(CAS Res.No.: 113981-44-5) hydrochloride;
(4) cefpirome(CAS Res.No.: 98753-19-6) sulfate;
(5) cefepime (CAS Res.No.: 123171-59-5) hydrochloride;
(6) cefoselis (CAS Res.No.: 122841-10-5) sulfate;
(7) cefotiam hexetil (CAS Res.No. 95789-30-3) hydrochloride;
(8) cefetamet pivoxil (CAS Res.No.: 65052-63-3) hydrochloride;
(9) cefcapene pivoxil (CAS Res.No.: 135889-00-8) hydrochloride;
(10) talampicillin (CAS Res.No.: 39878-70-1) hydrochloride;
(11) bacampicillin (CAS Res.No.: 37661-08-8) hydrochloride
(12) lenampicillin (CAS Res.No.: 80734-02-7) hydrochloride;
(13) pivmecillinam (CAS Res.No.: 32886-97-8) hydrochloride; and
(14) (1R,5S,6S)-6-[(R)-1-hydroxyethyl]-1-methyl-2-{(2S, 4S)-2-[(3R)-pyrrolidine-3-yl-(R)-hydroxy]methyl}pyrrolidine-4-ylthio]-1-carbapen-2-em-3-carboxylic acid.hydrochloride (JP-A 8-73462, Example 9).

Next, the basic antibiotic.oxalate (II) according to the present invention is a starting material for producing the above-mentioned basic antibiotic.inorganic acid salt (I) by salt-exchange, and specific examples thereof include an oxalate of the above-mentioned basic antibiotic.

Next, the alkali earth metal salt (III) of the inorganic acid according to the present invention is not limited so long as it is an adduct salt made from the inorganic acid and an alkali earth metal such as beryllium, magnesium, calcium, strontium and barium. Preferred are alkali earth metal halide (IV) and alkali earth metal sulfides (V).

More specific examples of the alkali earth metal halides (IV) include beryllium fluoride, magnesium fluoride, calcium fluoride, strontium fluoride, barium fluoride, beryllium chloride, magnesium chloride, calcium chloride, strontium chloride, barium chloride, beryllium bromide, magnesium bromide, calcium bromide, strontium bromide, barium bromide, beryllium iodide, magnesium iodide, calcium iodide, strontium iodide, barium iodide etc.

Among these, magnesium chloride, calcium chloride, magnesium bromide, calcium bromide etc. are more preferred.

Examples of the alkali earth metal sulfates (V) include beryllium sulfate, magnesium sulfate and calcium sulfate.

The following will describe the process for producing the compound of the present invention in more detail. (See the following chemical reaction formula, wherein the ring A means a basic antibiotic; $R^{10}$ means a protected functional group used in organic synthesis; Ak—E means an alkali earth metal; and B means an inorganic acid.)

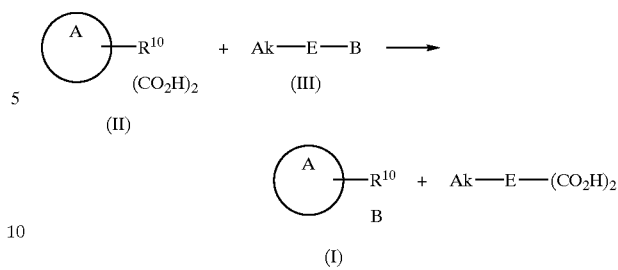

(1) Step 1

The present step is a deprotection reaction in the case that a basic antibiotic.oxalate has a protected functional group in the molecule thereof.

The protected function group herein means a group obtained by protecting a functional group, such as a hydroxyl group, an amino group or a carboxyl group, and used in organic synthesis. The deprotection reaction can be conducted in an ordinary manner such as hydrolysis or reduction.

(2) Step 2

The present step is subjecting the basic antibiotic.oxalate (II) to salt-exchange with an alkali earth metal salt (III) of an inorganic acid, to give the target basic antibiotic.inorganic acid salt (I).

Herein, the amount of the alkali earth metal salt (III) of the inorganic acid used is not limited and is usually from 0.7 to 2.0 equivalents, preferably from 0.8 to 1.5 equivalent, and more preferably from 0.9 to 1.3 equivalent.

Herein, the solvent used is not limited. Specific examples thereof include water, lower alcohols, ketone solvents, ester solvents, ether solvents, formamide solvents and dimethylsulfoxide. These may be used alone or in the form of a mixture thereof. Among these, water and lower alcohols are preferred.

The manner of carrying out (operating) the salt-exchange is not limited. Usually, a solution wherein a necessary amount of the alkali earth metal salt (III) of the inorganic acid is dissolved is dropwise added to a solution of the basic antibiotic.oxalate (II).

Herein, a solvent wherein an alkali earth metal.oxalate which is by-produced by the salt-exchange is insoluble is selected at this time, the alkali earth metal.oxalate is precipitated and can easily be obtained by filtration. Therefore, this case is more suitable for industry.

The target basic antibiotic.inorganic acid salt (I) is in a solution state at this stage. Accordingly, extracting operation is necessary. However, by concentration of the solvent or addition of a poor solvent (solvent having low solubility), it can easily be precipitated as crystal.

In the case of concentrating the solvent, it may be completely dried. It is however allowable to concentrate it partially into a small-amount solution, cool the resultant solution or cause the resultant solution to stand still, thereby precipitating the target crystals.

In the case of using the poor solvent, the kind thereof is not limited. In general, methanol, n-propanol, isopropanol etc. are preferred.

In the present invention, the step 2 may be performed after the step 1 is performed to isolate and/or purify the basic antibiotic.oxalate (II). However, the steps 1 and 2 may be continuously performed by the so-called one-spot reaction.

In this case, the deprotection reaction solution can be used, as it is, for the salt-exchange. As a result, column chromatography, pH adjustment and freeze-drying become unnecessary. Therefore, this case is excellent in industrial operability, reduction in production costs, processing in large amount and environment protection.

(1R,5S,6S)-6-[(R)-1-hydroxyethyl]-1-methyl-2-{(2S,4S)-2-[(3R)-pyrrolidine-3-yl-(R)-hydroxy]methyl}pyrrolidine-4-ylthio]-1-carbapen-2-em-3-carboxylic.acidoxalate (II-IX) according to the present invention, which is represented by the following formula:

(II-IX)

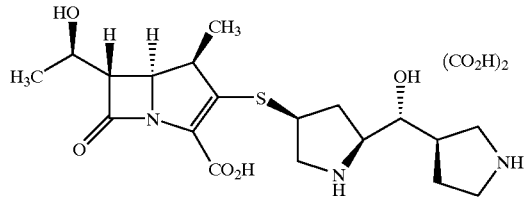

is a novel compound and is useful for a production intermediate.

Herein, the oxalate (II-I) of the carbapenem compound according to the present invention is represented by the following formula.

(II-I)

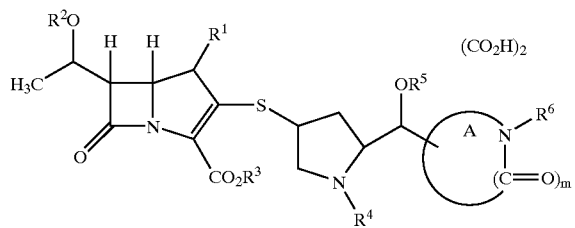

Wherein the ring A represents a 3- to 7-membered ring having at least one nitrogen atom, and the ring A may be substituted with other than $R^6$; $R^1$ represents hydrogen or methyl group; R2 and $R^5$ are the same as or different from each other and each represents hydrogen or a hydroxyl-protecting group; $R^3$ represents a carboxyl-protecting group; $R^4$ represents hydrogen, a lower alkyl group or an amino-protecting group; $R^6$ represents (1) hydrogen, (2) an optionally protected hydroxyl group, carbamoyl, formimidoyl, acetoimidoyl or a lower alkyl group which may be substituted with a substituent represented by the formula:

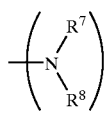

(wherein $R^7$ and $R^8$ are the same as or different from each other and each represents hydrogen, a lower alkyl group or an amino-protecting group) or (3) an amino-protecting group or an imono-protecting group; and m is 0 or 1.

In the above-mentioned definition, the hydroxyl-protecting group, the carboxyl-protecting group, the lower alkyl group, the amino-protecting group, the optionally protected hydroxyl, the imino-protecting group etc. are not limited so long as they are groups which are usually used in organic synthesis. More specific examples thereof include the same groups as described in JP-A 8-73462.

The oxalate (II-I) of the carbapenem compound according to the present invention has an asymmetric carbon atom or a double bond in the molecule thereof, and is in the form of an optically active substance, a diastereomer, or a racemic body. In the present invention, it is not limited and may be any one. About geometrical isomers thereof, the same matter is true.

More specific examples of the oxalate (II-I) of the carbapenem compound according to the present invention include the following compounds, though it is not limited thereto.

(1) p-Nitrobenzyl 6-(1-hydroxyethyl)-1-methyl-2-{[2-(azetidin-3-yl)hydroxymethylpyrrolidine-4-yl]thio}-1-carbapen-2-em-3-carboxylate.oxalate;

(2) p-nitrobenzyl 6-(1-hydroxyethyl)-1-methyl-2-{[2-(pyrrolidine-3-yl)hydroxymethylpyrrolidine-4-yl]thio}-1-carbapen-2-em-3-carboxylate.oxalate;

(3) p-nitrobenzyl 6-(1-hydroxyethyl)-1-methyl-2-{[2-(piperidine-3-yl)hydroxymethylpyrrolidine-4-yl]thio}-1-carbapen-2-em-3-carboxylate.oxalate;

(4) p-nitrobenzyl 6-(1-hydroxyethyl)-1-methyl-2-{[2-(piperidine-4-yl)hydroxymethylpyrrolidine-4-yl]thio}-1-carbapen-2-em-3-carboxylate.oxalate; and (5) p-nitrobenzyl 6-(1-hydroxyethyl)-1-methyl-2-{[2-(azepin-3-yl)hydroxymethylpyrrolidine-4-yl]thio}-1-carbapen-2-em-3-carboxylate.oxalate.

Next, 6-(1-hydroxyethyl)-1-methyl-2-{[2-(pyrrolidine-3-yl)hydroxymethylpyrrolidine-4-yl]thio}-1-carbapen-2-em-3-carboxylate.oxalate (II-II) according to the present invention is represented by the following formula:

(II-II)

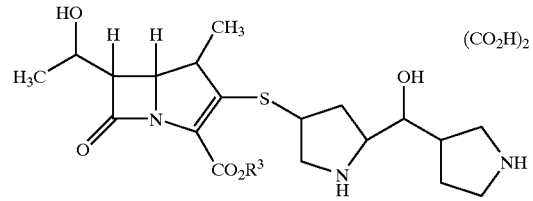

wherein $R^3$ represents a carboxyl-protecting group.

Lastly, p-nitrobenzyl(1R,5S,6S)-6-[(R)-1-hydroxyethyl]-1-methyl-2-{(2S,4S)-2-[(3R)-pyrrolidine-3-yl-(R)-hydroxy]methyl}pyrrolidine-4-ylthio]-1-carbapen-2-em-3-carboxylate.oxalate (II-III) according to the present invention is represented by the following formula:

(II-III)

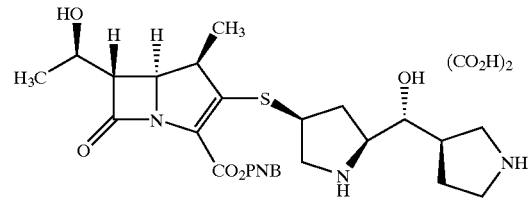

wherein PNB represents p-nitrobenzyl group.

Sequentially, p-nitrobenzyl(1R,5S,6S)-6-[(R)-1-hydroxyethyl]-1-methyl-1-carbapen-2-em-3-carboxylate-2-active compound (XIV) which is a starting material for p-nitrobenzyl(1R,5S,6S)-6-[(R)-1-hydroxyethyl]-1-methyl-2-{(2S,4S)-2-[(3R)-pyrrolidine-3-yl-(R)-hydroxy]methyl}pyrrolidine-4-ylthio]-1-carbapen-2-em-3- carboxylate.oxalate (II-III) according to the present invention, is represented by the following formula:

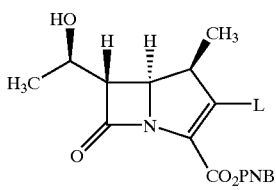

(XIV)

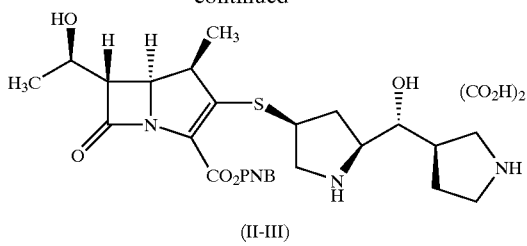

(II-III)

(wherein PNB has the same meaning as described above; L represents a leaving group which is usually used in organic synthesis, and specific examples thereof include trifluoroacethoxy, methanesulfonyloxy, trifluoromethanesulfonyloxy, p-toluenesulfonyloxy and diphenoxyphosphoryloxy), and can be produced by the process ([0069]–[0076]) described in JP-A 8-73462.

Furthermore, (2S,4S)-2-[[(3R)-pyrrolidine-3-yl-(R)-hydroxy]methyl]-4-mercaptopyrrolidine.dihydrochloride (XV), which is a reaction reagent, is represented by the following formula, and can be produced by the process described in Example 3 of JP-A 8-73462 etc.

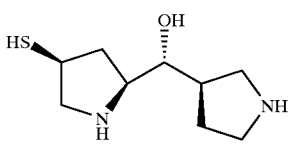

(XV)

The following will describe the process for producing the compound of the present invention in more detail. (See the following chemical reaction formula, wherein PNB and L have the same meanings as described above.)

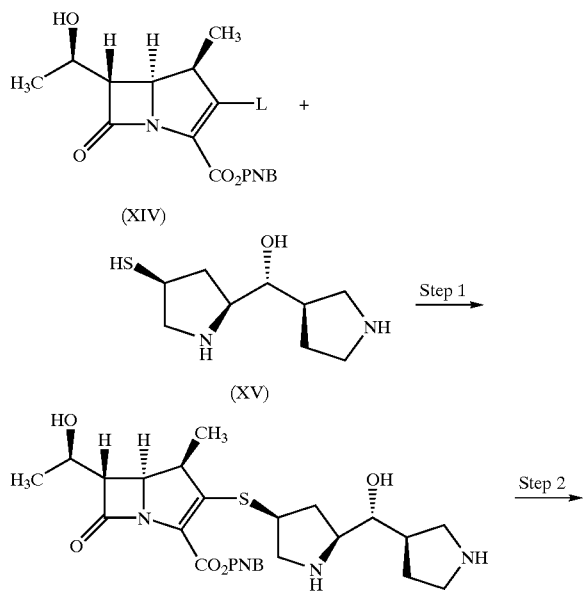

(1) Step 1

The present step is a step of reacting p-nitrobenzyl(1R, 5S,6S)-6-[(R)-1-hydroxyethyl]-1-methyl-1-carbapen-2-em-3-carboxylate-2-active compound (XIV) with (2S,4S)-2-[[(3R)-pyrrolidine-3-yl-(R)-hydroxy]methyl]-4-mercaptopyrrolidine.dihydrochloride (XV), to give a free compound or p-nitrobenzyl(1R,5S,6S)-6-[(R)-1-hydroxyethyl]-1-methyl-2-{(2S,4S)-2-[(3R)-pyrrolidine-3-yl-(R)-hydroxy]methyl}pyrrolidine-4-ylthio]-1-carbapen-2-em-3-carboxylate.

The present reaction is not limited so long as it is a thioether-synthesizing process which is usually conducted in organic synthesis. The process can easily be conducted in the presence of a base so as to give a high yield.

The kind of the base used herein is not limited. Specific examples thereof include alkali metal hydroxides such as sodium hydroxide and potassium hydroxide; alkali earth metal hydroxides such as barium hydroxide and calcium hydroxide; alkali metal carbonates such as sodium carbonate and potassium carbonate; alkali metal hydrogencarbonates such as sodium hydrogencarbonate and potassium hydrogencarbonate; inorganic bases such as alkali metal hydrides, for example, sodium hydride; primary to tertiary organic amines such as triethylamine, diethylamine, N,N-diisopropylamine and ethylamine; aromatic amines such as pyridine; and aniline derivatives such as N,N-dimethylaniline. Among these, N,N-diisopropylamine is more preferred.

(2) Step 2

The present step is a step of converting the free compound of p-nitrobenzyl(1R,5S,6S)-6-[(R)-1-hydroxyethyl]-1-methyl-2-{(2S,4S)-2-[(3R)-pyrrolidine-3-yl-(R)-hydroxy] methyl}pyrrolidine-4-ylthio]-1-carbapen-2-em-3-carboxylate into an oxalate thereof, to give the target p-nitrobenzyl(1R,5S,6S)-6-[(R)-1-hydroxyethyl]-1-methyl-2-{(2S,4S)-2-[(3R)-pyrrolidine-3-yl-(R)-hydroxy] methyl}pyrrolidine-4-ylthio]-1-carbapen-2-em-3-carboxylate.oxalate (II-III).

The present step can be conducted in a conventional way for conversion to oxalates. Usually, 0.7 to 2.0 equivalents of oxalic acid, preferably 0.8 to 1.5 equivalent of oxalic acid, and more preferably 0.9 to 1.2 equivalent of oxalic acid is dissolved into a solvent such as dimethylsulfoxide (DMSO), and then the resulting crystals were collected by filtration. Though the resulting crystals have sufficient purity by only air-drying, a higher-purity product can be obtained by solvent-washing, recrystallization etc.

Now, Examples are shown below to describe the present invention specifically. However, it is needless to say that the present invention is not limited thereto.

EXAMPLE 1

Production of (1R,5S,6S)-6-[(R)-1-hydroxyethyl]-1-methyl-2-{(2S,4S)-2-[(3R)-pyrrolidine-3-yl-(R)-hydroxy]methylpyrrolidine-4-yl}thio-1-carbapen-2-em-3-carboxylic acid.hydrochloride (calcium chloride: 1 equivalent)

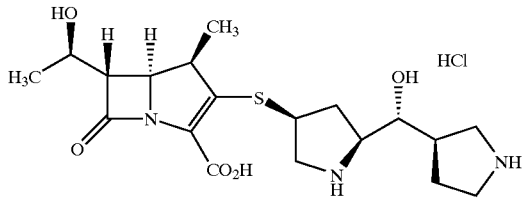

1-1) Deprotection (Reduction)

Into a reaction vessel having a pH-stat were charged p-nitrobenzyl(1R,5S,6S)-6-[(R)-1-hydroxyethyl]-1-methyl-2-{(2S,4S)-2-[(3R)-pyrrolidine-3-yl-(R)-hydroxy]methylpyrrolidine-4-yl}thio-1-carbapen-2-em-3-carboxylate.1 oxalate (26.0 g, 38.3 mmol), 20% palladium hydroxide-carbon (5.24 g, a 50% wet body) and water (598 ml) and then the mixture was suspended and stirred under cooling in an ice bath. The pH of the suspension was 3.81. After purge with nitrogen was performed 5 times, a 1 N sodium hydroxide solution was dropwise added thereto from a constant rate pump connected to a ph-stat under the atmosphere of hydrogen (normal pressure, supply of hydrogen from a balloon). The reaction solution was vigorously stirred for 3.5 hours while the pH thereof was adjusted to 5.5. The advance of the reaction was confirmed by HPLC. When the consumption (about 124 mL) of the 1 N sodium hydroxide stopped, purge with nitrogen was performed. Celite (26 g) was charged therein under stirring. The reaction solution was stirred for 7 minutes. The reaction solution was subjected to filtration under reduced pressure through Buchner funnel, on the bottom of which celite (78 g) was laid. The cake was washed with water (169 mL), to give an aqueous solution (790.7 g) of (1R,5S,6S)-6-[(R)-1-hydroxyethyl]-1-methyl-2-{(2S,4S)-2-[(3R)-pyrrolidine-3-yl-(R)-hydroxy]methylpyrrolidine-4-yl}thio-1-carbapen-2-em-3-carboxylic acid.oxalate. The quantitative analysis by HPLC demonstrated that the resultant aqueous solution contained 13.08 g of the free form of the title compound (yield: 82.9%).

1-2) Salt-exchange

To a part (28 g, containing 0.421 g of (1R,5S,6S)-6-[(R)-1-hydroxyethyl]-1-methyl-2-{(2S,4S)-2-[(3R)-pyrrolidine-3-yl-(R)-hydroxy]methylpyrrolidine-4-yl}thio-1-carbapen-2-em-3-carboxylic acid.oxalate) of this aqueous solution was dropwise added 1.6 g (about 1 equivalent) of 7.5% (w/w) calcium chloride solution (solution wherein 7.5 g of calcium chloride was dissolved in100 g of ion-exchanged water). The reaction solution immediately became whitely turbid. The precipitation was filtered off, to give a clear solution. Isopropanol (IPA, 120 mL) was added thereto so as to yield crystals. The precipitated crystals were collected by filtration and dried in a nitrogen stream for about 1 hour, to give the title compound as crystals (0.30 g, 0.248 g in terms of the free form).

$^1$H-NMR(400 MHz,$D_2O$); δ (ppm) 1.18(3H,d,J=7 Hz), 1.24(3H,d,J=6 Hz), 1.73(1H,td,J=9,13 Hz), 1.84(1H,ddd,J=7,10,12 Hz), 2.07–2.18(1H,m), 2.44(1H,qd,J=9,18 Hz), 2.58 (1H,td,J=8,14 Hz), 3.15(1H,dd,J=10,12 Hz), 3.21–3.37(3H,m), 3.39–3.47(2H,m), 3.51(1H,dd,J=8,12 Hz), 3.64(1H,dd, J=7,12 Hz), 3.83(1H,ddd,J=3,8,11 Hz), 3.92–4.01(2H,m), 4.15–4.23(2H,m).

EXAMPLE 2

Production of (1R,5S,6S)-6-[(R)-1-hydroxyethyl]-1-methyl -2-{(2S,4S)-2-[(3R)-pyrrolidine-3-yl-(R)-hydroxy]methylpyrrolidine-4-yl}thio-1-carbapen-2-em-3-carboxylic acid.hydrochloride (calcium chloride: 1.15 equivalent)

2-1) Deprotection (Reduction)

Into a reaction vessel having a pH-stat were charged p-nitrobenzyl(1R,5S,6S)-6-[(R)-1-hydroxyethyl]-1-methyl-2-{(2S,4S)-2-[(3R)-pyrrolidine-3-yl-(R)-hydroxy]methylpyrrolidine-4-yl}thio-1-carbapen-2-em-3-carboxylate.1 oxalate (4.0 g, 6.02 mmol), 20% palladium hydroxide-carbon (0.82 g, a 50% wet body) and water (92 ml), and then the mixture was suspended and stirred, under cooling in an ice bath. The pH of the suspension was 3.77. After purge with nitrogen was performed 5 times, a 1N sodium hydroxide solution was dropwise added thereto from a constant rate pump connected to a pH-stat under the atmosphere of hydrogen (normal pressure, supply of hydrogen from a balloon). The reaction solution was vigorously stirred for 3 hours while the pH thereof was adjusted to 5.5. The advance of the reaction was confirmed by HPLC. When the consumption (about 8.6 mL) of the 1 N sodium hydroxide stopped, purge with nitrogen was performed. Celite (4 g) was charged therein under stirring. The reaction solution was stirred for 7 minutes. The reaction solution was subjected to filtration under reduced pressure through Buchner funnel, on the bottom of which Celite (12 g) was laid. The cake was washed with water (26 mL) to give an aqueous solution (109.9 g) of (1R,5S,6S)-6-[(R)-1-hydroxyethyl]-1-methyl-2-{(2S,4S)-2-[(3R)-pyrrolidine-3-yl-(R)-hydroxy]methylpyrrolidine-4-yl}thio-1-carbapen-2-em-3-carboxylic acid.oxalate. The quantitative analysis by HPLC demonstrated that the resultant aqueous solution contained 1.88 g of the free form of the title compound (yield: 75.7%).

2-2) Salt-exchange

To a part (75 g, containing 1.193 g of (1R,5S,6S)-6-[(R)-1-hydroxyethyl]-1-methyl-2-{(2S,4S)-2-[(3R)-pyrrolidine-3-yl-(R)-hydroxy]methylpyrrolidine-4-yl}thio-1-carbapen-2-em-3-carboxylic acid.oxalate) of this solution was dropwise added 5.287 g (about 1.15 equivalent) of 7.5% (w/w) calcium chloride solution (solution wherein 7.5 g of calcium chloride was dissolved in 100 g of ion-exchanged water). The reaction solution became whitely turbid rapidly. The resulting precipitates were filtered off, to give a clear solution. The solution was concentrated into about ½ of the original volume thereof. Isopropanol (88 mL) was added thereto so as to give crystals. The precipitated crystals were collected by filtration and dried in a nitrogen stream for about 1 hour, to give the title compound as crystals (1.222 g, 1.0416 g in terms of the free form).

EXAMPLE 3

Production of (1R,5S,6S)-6-[(R)-1-hydroxyethyl]-1-methyl-2-{(2S,4S)-2-[(3R)-pyrrolidine-3-yl-(R)-hydroxy]methylpyrrolidine-4-yl}thio-1-carbapen-2-em-3-carboxylic acid.hydrochloride (calcium chloride: 1.25 equivalent)

3-1) Deprotection (Reduction)

Into a reaction vessel having a pH-stat were charged p-nitrobenzyl(1R,5S,6S)-6-[(R)-1-hydroxyethyl]-1-methyl-2-{(2S,4S)-2-[(3R)-pyrrolidine-3-yl-(R)-hydroxy]methylpyrrolidine-4-yl}thio-1-carbapen-2-em-3-carboxylate.oxalate (5.0 g, 7.31 mmol), 20% palladium hydroxide-carbon (0.99 g, a 50% wet body) and water (115 ml), and then the mixture was suspended and stirred, under cooling in an ice bath. The pH of the suspension was 3.75. After purge with nitrogen was performed 5 times, an 1 N sodium hydroxide solution was dropwise added thereto from a constant rate pump connected to a pH-stat under the atmosphere of hydrogen (normal pressure, supply of hydrogen from a balloon). The reaction solution was vigorously stirred for 2.5 hours while the pH thereof was adjusted to 5.5. The advance of the reaction was confirmed by HPLC. When the consumption (about 8.3 mL) of the 1N sodium hydroxide stopped, purge with nitrogen was performed. Celite (5 g) was charged therein under stirring. The reaction solution was stirred for 7 minutes, and then subjected to filtration under reduced pressure through Buchner funnel, on the bottom of which Celite (15 g) was laid. The cake was washed with water (32.5 mL), to give an aqueous solution (147.8 g) of (1R,5S,6S)-6-[(R)-1-hydroxyethyl]-1-methyl-2-{(2S,4S)-2-[(3R)-pyrrolidine-3-yl-(R)-hydroxy]methylpyrrolidine-4-yl}thio-1-carbapen-2-em-3-carboxylic acid/oxalate. The quantitative analysis by HPLC demonstrated that the resultant aqueous solution contained 2.36 g of the free form of the title compound (yield: 78.4%).

3-2) Salt-exchange

To a part (112.9 g, containing 1.73 g of (1R,5S,6S)-6-[(R)-1-hydroxyethyl]-1-methyl-2-{(2S,4S)-2-[(3R)-pyrrolidine-3-yl-(R)-hydroxy]methylpyrrolidine-4-yl}thio-1-carbapen-2-em-3-carboxylic acid.oxalate) of this solution was dropwise added 7.78 g (about 1.25 equivalent) of 7.5% (w/w) calcium chloride solution (solution wherein 7.5 g of calcium chloride was dissolved in 100 g of ion-exchanged water). The reaction solution became whitely turbid rapidly. The precipitation was filtered off to give a clear solution. This solution was concentrated into about ½ of the original volume thereof. Isopropanol (75.3 mL) was added thereto so as to give crystals. The precipitated crystals were collected by filtration, and dried in a nitrogen stream for about 1 hour, to give the title compound as crystals (1.925 g, 1.562 g in terms of the free form).

EXAMPLE 4

Production of (1R,5S,6S)-6-[(R)-1-hydroxyethyl]-1-methyl-2-{(2S,4S)-2-[(3R)-pyrrolidine-3-yl-(R)-hydroxy]methylpyrrolidine-4-yl}thio-1-carbapen-2-em-3-carboxylic acid.oxalate

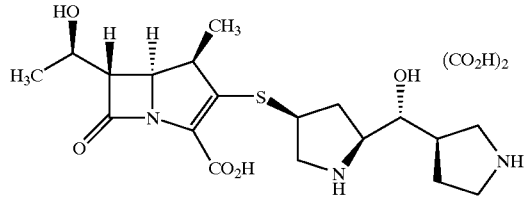

4-1) Deprotection (Reduction)

Into a reaction vessel having a pH-stat were charged p-nitrobenzyl(1R,5S,6S)-6-[(R)-1-hydroxyethyl]-1-methyl-2-{(2S,4S)-2-[(3R)-pyrrolidine-3-yl-(R)-hydroxy]methylpyrrolidine-4-yl}thio-1-carbapen-2-em-3-carboxylate.oxalate (5.0 g, 7.12 mmol), 20% palladium hydroxide-carbon (0.97 g, a 50% wet body) and water (115 ml). Then the mixture was suspended and stirred under cooling in an ice bath. The pH of the suspension was 3.7. After purge with nitrogen was performed 5 times, an 1 N sodium hydroxide solution was dropwise added thereto from a constant rate pump connected to a pH-stat under the atmosphere of hydrogen (normal pressure, supply of hydrogen from a balloon). The reaction solution was vigorously stirred for 2 hours while the pH thereof was adjusted to 5.5. The advance of the reaction was confirmed by HPLC. When the consumption (about 8.3 mL) of the 1 N sodium hydroxide stopped, purge with nitrogen was performed. Celite (5 g) was charged therein under stirring. The reaction solution was stirred for 7 minutes. The reaction solution was subjected to filtration under reduced pressure with a Buchner funnel, on the bottom of which celite (15 g) was laid. The cake was washed with water (32.5 mL), to give an aqueous solution (154.7 g) of the title compound. The quantitative analysis by HPLC demonstrated that the resulting aqueous solution contained the title compound in a free form (2.43g, yield: 82.9%).

4-2) (Crystallization

To a part (25 g) of this solution were dropwise added methanol (200 mL) and isopropanol (30 mL) under stirring. The reaction solution was stirred under ice-cooling for 3 hours. The precipitated solid was filtered under reduced pressure, washed with methanol (10 mL) and dried under reduced pressure, to give the title compound as a slightly-yellowish white powder (the free form content: 67.9%, gradient HPLC purity: 98.9%).

$^1$H-NMR(400 MHz,D$_2$O); δ (ppm) 1.10(d,3H,J=7.3 Hz), 1.17(d,3H,J=6.4 Hz), 1.58–1.73(m,1H), 1.72–1.85(m,1H), 1.98–2.14(m,1H), 2.36(q-like,1H,J=8.3 Hz), 2.51(dt,1H,J=7.8,6.8 Hz), 3.09(dd,1H,J=9.0,12 Hz), 3.14–3.25(m,3H), 3.25–3.40(m,2H), 3.43(dd,1H,J=8.0,12 Hz), 3.55–3.65(m, 1H), 3.72–3.83(m,2H), 4.08–4.17(m,2H).

EXAMPLE 5 p-Nitrobenzyl(1R,5S,6S)-6-[(R)-1-hydroxyethyl]-1-methyl-2-{(2S,4S)-2-[(3R)-pyrrolidine-3-yl-(R)-hydroxy]methyl}pyrrolidine-4-ylthio]-1-carbapen-2-em-3-carboxylate.monooxalate

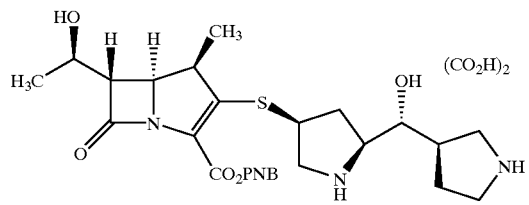

Wherein PNB represents p-nitrobenzyl group.

p-Nitrobenzyl(1R,5S,6S)-2-diphenoxyphosphoryloxy-6-[(R)-1-hydroxyethyl]-1-methyl-1-carbapen-2-em-3-carboxylate (50.0 g, 84.1 mmol) was dissolved in N,N-dimethylformamide (150 mL) and dimethylsulfoxide (300 mL) in a nitrogen stream, under stirring. After cooling to 10° C., N,N-diisopropylamine (36.6 mL, 210.3 mmol) was added thereto. Further, (2S,4S)-2-{[(3R)-pyrrolidine-3-yl-(R)-hydroxy]methyl}-4-mercaptopyrrolidine.dihydrochloride (25.46 g, 92.5 mmol) was added thereto, followed by stirring for 2 hours. A solution of oxalic acid (7.8 g, 86.6 mmol) in dimethylsulfoxide (30 mL) was added to the reaction solution, so that a solid was precipitated. Furthermore, 2-propanol (1750 mL) was added thereto, followed by stirring at the same temperature for 4 hours. The reaction solution in a slurry form was subjected to filtration under reduced pressure through Buchner funnel, and air-dried in a nitrogen stream for 1 hour, to give 117.4 g of a wet product. This product was suspended into methanol (333 mL) and ethanol (667 mL) under stirring at 14° C. for 15 hours. The solid was collected by filtration and dried under reduced pressure for 20 hr, to give the title compound (52.3 g, yield: 92%).

¹H-NMR(400 MHz,DMSO-d₆); δ (ppm) 1.15(d,1H,J=6.3 Hz), 1.46(d,1H,J=7.6 Hz), 1.52(dt,1H,J=13,8.8 Hz), 1.64 (dq,1H,J=12,9 Hz), 1.87–1.98(m,1H), 2.23–2.40(m,2H), 2.80(dd,1H,J=6,12 Hz), 2.92–3.10(m,2H), 3.12–3.30(m,3H), 3.30–3.56(m,3H, 3.73(quintet-like,1H,J=6.6 Hz),3.97 (quintet-like,1H,J=6.3 Hz), 4.22(dd,1H,J=5.4,9.5 Hz), 5.36 (ABq,2H,J=14 Hz), 7.71(d,2H,J=8.5 Hz), 8.23(d,2H,J=8.5 Hz).

What is claimed is:

1. A process for producing a basic antibiotic.inorganic acid salt (I) wherein the basic antibiotic.inorganic acid salt (I) is selected from the group consisting of:
   (1) cefotiam hydrochloride;
   (2) cefmenoxime hydrochloride;
   (3) cefozopran hydrochloride;
   (4) cefpirome sulfate;
   (5) cefepime hydrochloride;
   (6) cefoselis sulfate;
   (7) cefotiam hexetil hydrochloride;
   (8) cefetamet pivoxil hydrochloride;
   (9) cefcapene pivoxil hydrochloride;
   (10) talampicillin hydrochloride;
   (11) bacampicillin hydrochloride;
   (12) lenampicillin hydrochloride;
   (13) pivmecillinam hydrochloride; and
   (14) (1R,5S,6S)-6-[(R)-1-hydroxyethyl]-1-methyl-2-{(2S,4S)-2-[(3R)-pyrrolidine-3-yl-(R)-hydroxy]methyl}pyrrolidine-4-ylthio]-1-carbapen-2-em-3-carboxylic acid.hydrochloride, said process comprising:
      subjecting a basic antibiotic.oxalate (II) to salt-exchange with an alkali earth metal salt (III) of an inorganic acid:

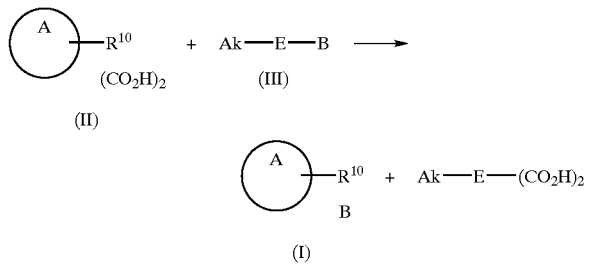

wherein the ring A represents the basic antibiotic; R¹⁰ represents a protected functional group; Ak—E represents the alkali earth metal; and B represents the inorganic acid; and
producing said basic antibiotic.inorganic acid salt (I).

2. The process for producing the basic antibiotic.inorganic acid salt (I) according to claim 1, wherein the alkali earth metal salt (III) of the inorganic acid is an alkali earth metal halide (IV) or an alkali earth metal sulfate (V).

3. The process for producing the basic antibiotic.inorganic acid salt (I) according to claim 1, wherein the alkali earth metal halide (IV) is selected from the group consisting of beryllium fluoride, magnesium fluoride, calcium fluoride, strontium fluoride, barium fluoride, beryllium chloride, magnesium chloride, calcium chloride, strontium chloride, barium chloride, beryllium bromide, magnesium bromide, calcium bromide, strontium bromide, barium bromide, beryllium iodide, magnesium iodide, calcium iodide, strontium iodide and barium iodide.

4. The process for producing the basic antibiotic.inorganic acid salt (I) according to claim 1, wherein the alkali earth metal sulfate (V) is selected from the group consisting of beryllium sulfate, magnesium sulfate and calcium sulfate.

5. A process for producing p-nitrobenzyl(1R,5S,6S)-6-[(R)-1-hydroxyethyl]-1-methyl-2-{(2S,4S)-2-[(3R)-pyrrolidine-3-yl-(R)-hydroxy]methyl}pyrrolidine-4-ylthio]-1-carbapen-2-em-3-carboxylate.oxalate (II-III), which comprises:
   reacting p-nitrobenzyl(1R,5S,6S)-6-[(R)-1-hydroxyethyl]-1-methyl-1-carbapen-2-em-3-carboxylate-2-active compound (XIV) represented by the following formula:

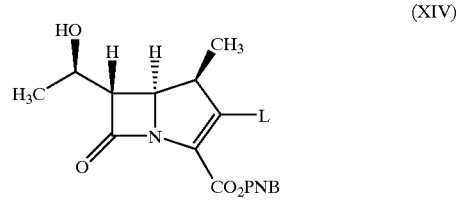

wherein PNB has the same meaning as described above; and L represents a leaving group, with (2S,4S)-2-{[(3R)-pyrrolidine-3-yl-(R)-hydroxy]methyl}-4-mercaptopyrrolidine.dihydrochloride (XV) represented by the following formula:

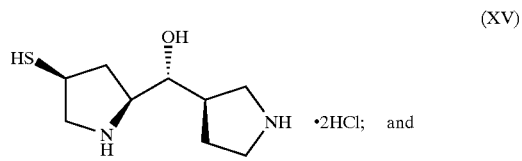

then converting the resultant into an oxalate.

6. The process for producing the basic antibiotic.inorganic acid salt (I) according to claim 1, wherein the amount of the alkali earth metal salt (III) of the inorganic acid is from 0.9 to 1.3 equivalents.

7. The process for producing the basic antibiotic.inorganic acid salt (I) according to claim 1, wherein water is the solvent when subjecting the basic antibiotic.oxalate (II) to salt-exchange with the alkali earth metal salt (III) of the inorganic acid.

8. p-Nitrobenzyl(1R,5S,6S)-6-[(R)-1-hydroxyethyl]-1-methyl-2-{(2S,4S)-2-[(3R)-pyrrolidine-3-yl-(R)-hydroxy]methyl}pyrrolidine-4-ylthio]-1-carbapen-2-em-3-carboxylate.oxalate (II-III) represented by the following formula:

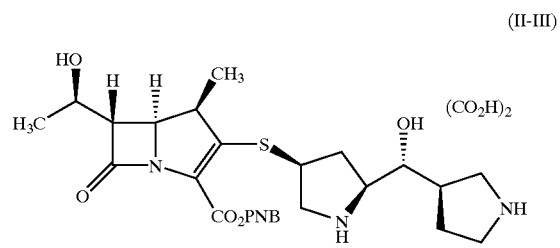

wherein PNB represents p-nitrobenzyl group.

9. (1R,5S,6S)-6-[(R)-1-hydroxyethyl]-1-methyl-2-{(2S,4S)-2-[(3R)-pyrrolidine-3-yl-(R)-hydroxy]methyl}pyrrolidine-4-ylthio]-1-carbapen-2-em-3- carboxylate-oxalate (II-IX) represented by the following formula:

(II-IX)

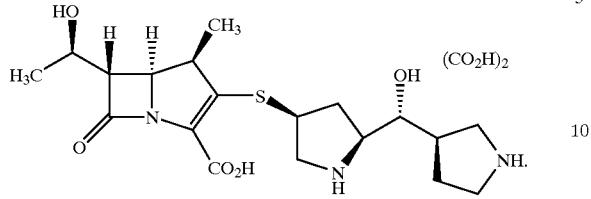

10. A process for producing (1R,5S,6S)-6-[(R)-1-hydroxyethyl]-1-methyl-2-{(2S,4S)-2-[(3R)-pyrrolidine-3-yl-(R)-hydroxy]methyl}pyrrolidine-4-ylthio]-1-carbapen-2-em-3-carboxylic acid.hydrochloride (VIII) represented by the following formula:

(VIII)

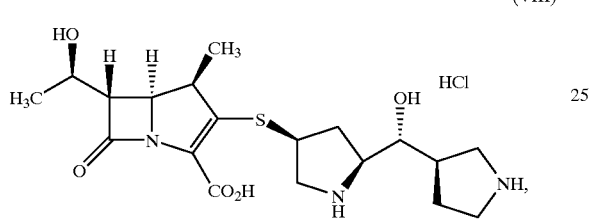

said method comprising:

subjecting a basic antibiotic protector-oxalate of p-nitrobenzyl(1R,5S,6S)-6-[(R)-1-hydroxyethyl]-1-methyl-2-{(2S,4S)-2-[(3R)-pyrrolidine-3-yl-(R)-hydroxy]methyl}pyrrolidine-4-ylthio]-1-carbapen-2-em-3-carboxylate.oxalate (VII) represented by the following formula:

(VII)

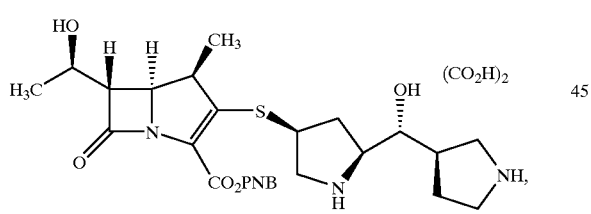

wherein PNB represents p-nitrobenzyl group, to deprotection reaction;

then subjecting to salt-exchange with calcium chloride;

then crystallizing the resultant after said salt-exchange by adding methanol and/or isopropanol; and to producing said basic (1R,5S,6S)-6-[(R)-1-hydroxyethyl]-1-methyl-2-{(2S,4S)-2-[(3R)-pyrrolidine-3-yl-(R)-hydroxy]methyl}pyrrolidine-4-ylthio]-1-carbapen-2-em-3-carboxylic acid.hydrochloride (VIII).

11. A process for producing a basic antibiotic.inorganic acid salt (I), said method comprising:

subjecting a basic antibiotic.oxalate (II) to salt-exchange with an alkali earth metal salt (III) of an inorganic acid:

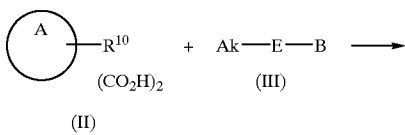

(II)

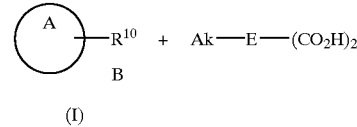

(I)

wherein the ring A represents the basic antibiotic; $R^{10}$ represents a protected functional group; Ak—E represents the alkali earth metal; and B represents the inorganic acid; and producing said basic antibiotic.inorganic acid salt (I);

wherein said basic antibiotic.oxalate (II) is an oxalate (II-I) of a carbapenem compound, represented by the following formula:

(II-I)

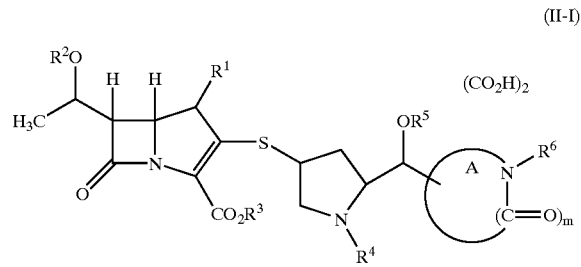

wherein the ring A means a 3- to 7-membered ring having at least one nitrogen atom;

$R^1$ represents hydrogen or methyl group;

$R^2$ and $R^5$ are the same as or different from each other and each represents hydrogen or a hydroxyl-protecting group;

$R^3$ represents a carboxyl-protecting group;

$R^4$ represents hydrogen, a lower alkyl group or an amino-protecting group; and $R^6$ represents (1) hydrogen, (2) an optionally protected hydroxyl group, carbamoyl, formimidoyl, acetoimidoyl or a lower alkyl group which may be substituted with a substituent represented by the formula:

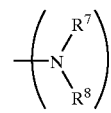

wherein $R^7$ and $R^8$ are the same as or different from each other and each represents hydrogen, a lower alkyl groups or an amino-protecting group, or (3) an amino-protecting group or an imino-protecting group; and m is 0 or 1.

12. An oxalate (II-I) of a carbapenem compound, represented by the following formula:

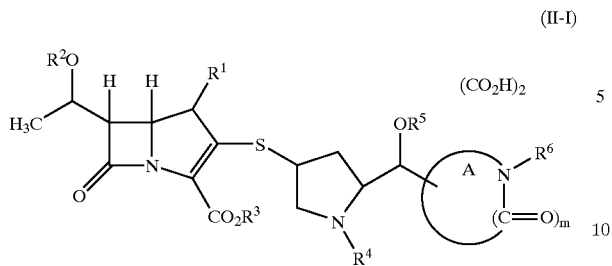

(II-I)

wherein the ring A represents a 3- to 7-membered ring having at least one nitrogen atom, and the ring A is optionally substituted with a substituent other than $R^6$;

$R^1$ represents hydrogen or methyl group;

$R^2$ and $R^5$ are the same as or different from each other and each represents hydrogen or a hydroxyl-protecting group;

$R^3$ represents a carboxyl-protecting group;

$R^4$ represents hydrogen, a lower alkyl group or an amino-protecting group;

$R^6$ represents (1) hydrogen, (2) an optionally protected hydroxyl group, carbamoyl, formimidoyl, acetoimidoyl or a lower alkyl group which may be substituted with a substituent represented by the formula:

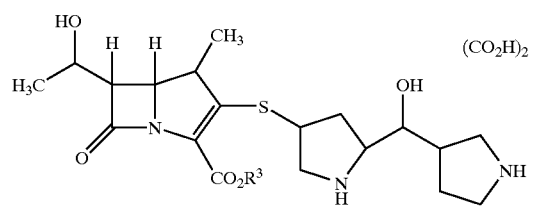

wherein $R^7$ and $R^8$ are the same as or different from each other and each represents hydrogen, a lower alkyl groups or an amino-protecting group, or (3) an amino-protecting group or an imino-protecting group; and m is 0 or 1.

13. 6-(1-Hydroxyethyl)-1-methyl-2-{[2-(pyrrolidine-3-yl)hydroxymethylpyrrolidine-4-yl]thio}-1-carbapen-2-em-3-carboxylic acid derivative.oxalate (II-II) represented by the following formula:

(II-II)

wherein $R^3$ represents a carboxyl-protecting group.

* * * * *

UNITED STATES PATENT AND TRADEMARK OFFICE
CERTIFICATE OF CORRECTION

PATENT NO.     : 6,642,377 B1
DATED          : November 4, 2003
INVENTOR(S)    : Kayano et al.

It is certified that error appears in the above-identified patent and that said Letters Patent is hereby corrected as shown below:

Title page,
Item [54], Title, please change from "PROCESS FOR THE PREPARATION OF BASIC ANTIBIOTIC-INORGANIC ACID ADDITION SALTS AND INTERMEDIATE OXALATES" to -- PROCESS FOR THE PREPARATION OF BASIC ANTIBIOTIC INORGANIC ACID ADDITION SALTS AND OXALATE INTERMEDIATE --.

Signed and Sealed this

Eighth Day of June, 2004

JON W. DUDAS
*Acting Director of the United States Patent and Trademark Office*